United States Patent [19]
Boyd

[11] Patent Number: 5,503,163
[45] Date of Patent: Apr. 2, 1996

[54] NEUROSURGICAL DRAPE PACK

[76] Inventor: Lynn Boyd, 19482 Summer Breeze La., Huntington Beach, Calif. 92648

[21] Appl. No.: 859,067

[22] Filed: Mar. 27, 1992

Related U.S. Application Data

[63] Continuation-in-part of Ser. No. 718,588, Jun. 20, 1991, abandoned.

[51] Int. Cl.$^6$ ......................................................... A61F 5/37
[52] U.S. Cl. ........................... 128/849; 128/852; 128/855
[58] Field of Search ..................................... 128/849–856

[56] References Cited

U.S. PATENT DOCUMENTS

| | | | |
|---|---|---|---|
| 3,503,391 | 3/1970 | Melges | 128/853 |
| 3,537,446 | 11/1970 | Rowland | 128/853 |
| 3,561,439 | 2/1971 | Bayer | 128/853 |
| 3,695,260 | 10/1972 | Endres | 128/853 |
| 3,750,664 | 8/1973 | Collins | 128/853 |
| 3,921,627 | 11/1975 | Wilson | 128/853 |
| 3,930,497 | 1/1976 | Krebs | 128/853 |
| 4,569,341 | 2/1986 | Morris | 128/853 |
| 4,586,498 | 5/1986 | Morris | 128/853 |
| 5,010,899 | 4/1991 | Thompson | 128/853 |

*Primary Examiner*—Michael A. Brown
*Attorney, Agent, or Firm*—Dennis W. Beech

[57] ABSTRACT

A surgical pack which is prefolded and packaged with the drape cover material necessary to create a sterile operating area for neurosurgery. The neurosurgical drape pack contains the normal table cover sheet, split sheet, craniotomy incise sheet and may include an absorbent drape all assembled, sterilized, and sealed. This package can be placed on the neurosurgery operating table where it is then opened and unfolded to specific edges of the table in preparation for the patient. Once the table is over the patient, the split sheet and craniotomy incise sheet can be positioned on the surgical incision area on the patient in only a few minutes. The drape pack provides for rapid preparation of the operating room environment and the patient thus saving many minutes of time that the patient must be anesthetized and operating personnel must wait to begin the operation. In a simple version of the drape pack only three of four drapes are packaged for easy placement and drape of the surgical site. In the more complex drape pack the bovie and bipolar connections and devices can be prepackaged as well as the suction tubes and heads can be prepackaged using channels and pockets in a manner which prevents their falling off the table. The craniotomy incise sheet can be fit with pockets to hold the surgical devices and suction tips.

16 Claims, 5 Drawing Sheets

NEUROSURGICAL DRAPE PACK

CROSS REFERENCES TO RELATED APPLICATIONS

This is a continuation-in-part of application Ser. No. 07/718,588 filed Jun. 20, 1991, now abandoned.

BACKGROUND OF THE INVENTION

1. Field of the Invention

This invention relates to an apparatus for use in keeping neurosurgical operating areas sterile during the surgical procedure. In particular, this apparatus relates to the neurosurgical table or other device which is used to position the surgical tools and drapes or sheets for use during the operation. The invention involves a surgical draping system combining several drapes and/or sheets to form a drape pack and additionally concerns methods for folding drape combinations as a compact pack for ease of handling and application.

2. Description of Prior Art

Currently in use are neurosurgical tables which normally are located over and slightly above the person on which the operation is to be performed. The table is usually prepared for the surgical procedure by the placement of several drapes and/or sheets, each for a specific purpose, in order to cover the non-sterile table and area surrounding the head of the patient on which the surgery is to be performed.

This preparation is performed by a nurse or other support

This preparation is performed by a nurse or other support person just prior to the actual performance of the surgery. There is no prepackaged apparatus or drape pack containing the minimum number of drapes or sheets to provide the necessary sterile fields to allow this procedure to be performed rapidly resulting in periods of ten to fifteen minutes or more of the operating room personnel, including the surgeon, standing around with the patient anesthetized while the nurse prepares the operating area.

The current general practice method is to take each drape or sheet that is individually assembled, sterilized, and packaged, and position them one at a time while the patient is anesthetized and under the table. Once the draping is completed, the surgical instruments and devices must be placed and positioned on the covered table. Additionally, electric cords and suction lines running from the patient's feet area along the sides of the table to the patient's head area are clamped or tied to the edges of the outer sheet on the table. These cords and lines can become entangled and when pulled may cause devices to fall to the floor and become unsterile. This represents a risk to the patient while under a general anesthesia for the period of time required for the preparation and in instances when new sterile devices are needed.

The present invention combines the necessary drapings and/or sheets and operating devices in a pre-packaged apparatus or drape pack which allows all elements to be quickly unfolded and properly placed in the operation area. All of the necessary elements are in one sealed and sterile package which when specifically placed on the neurosurgical table provide the ability to save 15 to 20 minutes of time in the operating room. Additionally, the electric cords and suction lines may be placed in channels formed on the outer sheet and positioned along the edges of the table top allowing the cords and lines to be completely covered eliminating any possibility of entanglement. This means the patient need not be under the general anesthesia as long and reduces the margin of error in making the operating environment stable.

SUMMARY OF THE INVENTION

A primary objective of the present invention is to reduce the critical time in the operating room when a neurosurgical patient is under general anesthesia. The prepared neurosurgical drape pack can be quickly positioned, unfolded and used to sterilize the operating area and to connect necessary surgical devices. A further object of the invention is to reduce the surgeon's and other operating personnel's time in the operating room. Another object of the drape pack is to reduce the chance for error in the sterilization of the operating environment which causes more delay or complications.

In accordance with the description presented herein, other objects of this invention will become apparent when the description and drawings are reviewed.

DESCRIPTION OF THE PREFERRED EMBODIMENT

Figure 1:
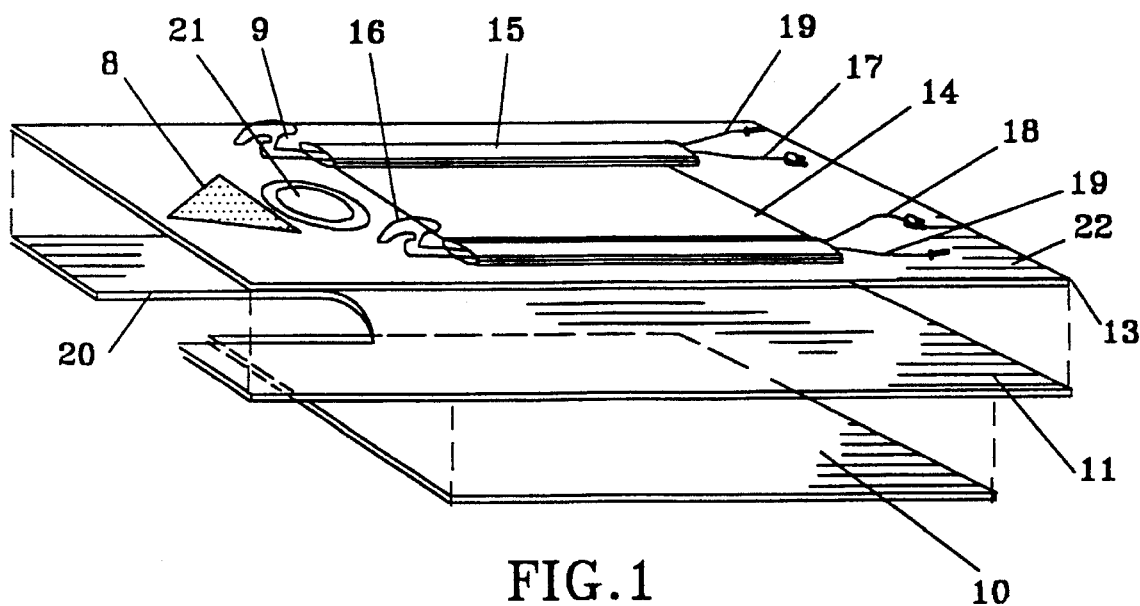
FIG. 1 is a perspective assembly view showing component parts and devices.

The neurosurgical drape pack consists of a table cover sheet, split sheet, and craniotomy incise sheet with two channels and two pockets. The drape pack may also include an absorbent drape. This combination is folded in a specific manner within a sterile package which presents the table cover as the outside most element. The items inside the package are sterilized with only the outer sealed cover exposed. This allows for quick placing of the pack at a specific location on the neurosurgical table, the unfolding of the pack for a sterile operating environment, and quick connection of operating instruments.

Referring to FIG. 1 through 6, the neurosurgical drape pack (7) consists of three independently constructed sheets or drapes, a table cover sheet (10), a split sheet (11), and a craniotomy incise sheet (13) arranged in order of final position when unfolded for the intended operation. The drape pack (7) can also be assembled with an absorbent drape (14) positioned on the craniotomy incise sheet (13). The craniotomy incise sheet (13) as understood in the art usually consists of a main sheet with a clear window (21) or fenestration for access to the operating site on the patient's skull. The craniotomy incise sheet (13) will also normally have an absorbent reinforcing area secured to the surface opposite the patient's skull surrounding the clear window (21) with a pocket (8) attached below the clear window (21) to collect fluids and other material. The pocket (8) in one configuration is U-shaped to fit around two sides of the clear window (21) to better collect fluids and material to the bottom of the pocket.

Figure 2:
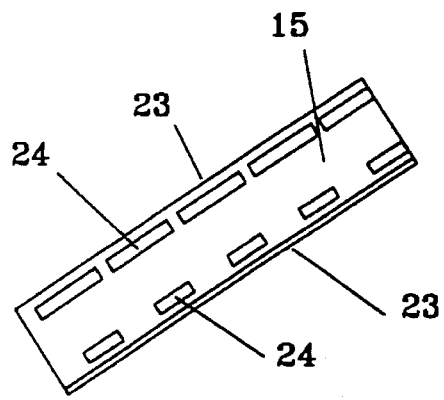
FIG. 2 illustrates the sheet of material and adhesive tape that forms the channel.
Figure 3:
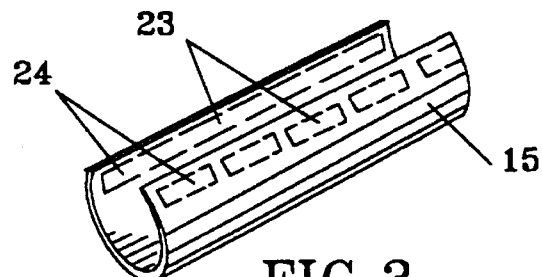
FIG. 3 illustrates the formation of the channels by wrapping the lower longitudinal edge up to the top longitudinal edge.
Figure 4:
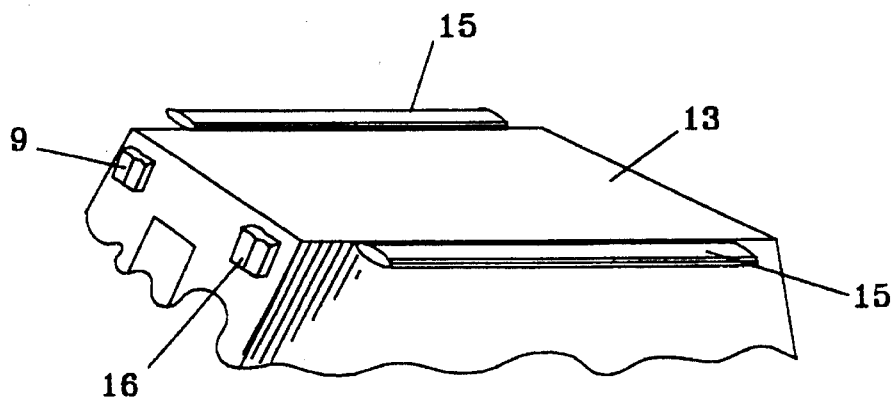
FIG. 4 illustrates the positions of the channels and pockets after the drapes are unfolded.

The craniotomy incise sheet (13) has two channels (15) or conduits formed from two or more strips, made of varying types of material, approximately the length of the neurosurgical overhead table (5) and approximately six to ten inches wide, FIGS. 2 and 3, secured to the outer surface (22) of the craniotomy incise sheet (13) and positioned so they hang just over the nurse edge (1) and side edge (3) of the table (5) when the drape pack (7) is unfolded as in FIG. 4. Each channel (15) has a longitudinal edge (23) attached to the craniotomy incise sheet (13) and a longitudinal edge (23) not attached. The longitudinal edges (23) have small strips of pressure sensitive self adhesive tape (24) for attachment. This allows the channel (15) to be formed after the drape pack (7) is unfolded by folding the channel (15) material at the unattached longitudinal edge (23) up to the nurse edge (1) and side edge (3) and applying the self adhesive tape (24) to contact and adhere to the craniotomy incise sheet (13) just below the nurse edge (1) and side edge (3). This allows operating room personnel to install the suction tubes (19) and electrical bipolar cord (17) and bovie cord (18) in the channels (15) at the time of operation as they see fit. The drape pack (7) may also be assembled so that each channel (15) is formed on the craniotomy incise sheet (13) and holds a suction tube (19) and an electrical bipolar cord (17) or a bovie cord (18) prior to the drape pack (7) being folded for final assembly.

The craniotomy incise sheet (13) can also have a bovie pocket (16) consisting of two compartments, each approximately three inches wide and six inches deep, which will hold a bovie device and a suction tip which are connected to the electrical bovie cord (18) and suction tube (19) respectively. On the opposite side of the patient on the craniotomy incise sheet (13) can be a bipolar pocket (9) consisting of two compartments the same size as the bovie pocket (16), which can hold the bipolar forceps and a suction tip which are connected to the electrical bipolar cord (17) and suction tube (19) respectively. Both pockets are designed to hang off the head edge (2) of the table (5) for easy access by operating personnel, FIG. 4.

Figure 5:
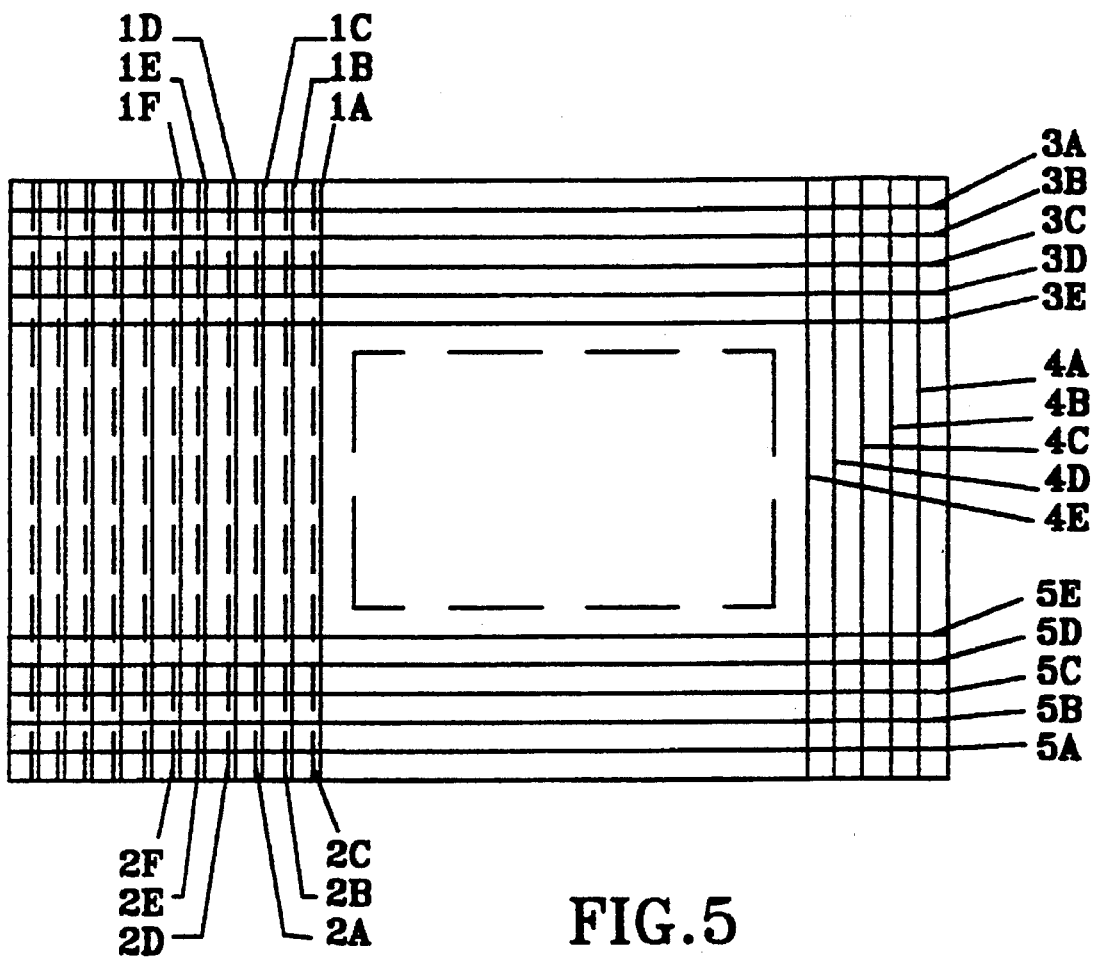
FIG. 5 is a top plan view detailing the folding lines and sequences.
Figure 9:
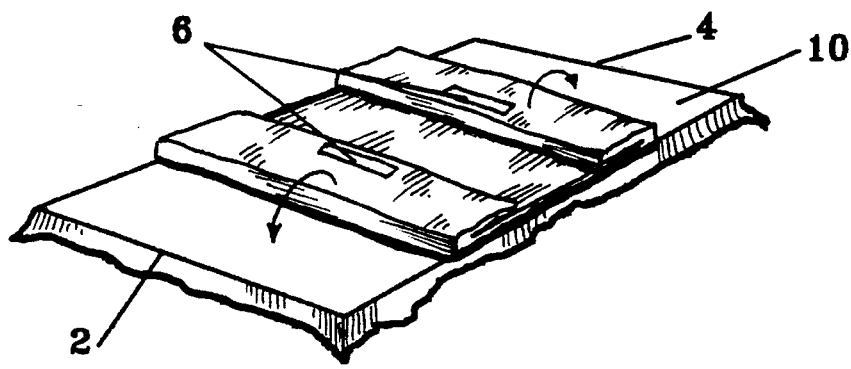
FIG. 9 illustrates the continuing unfolding in progression.
Figure 10:
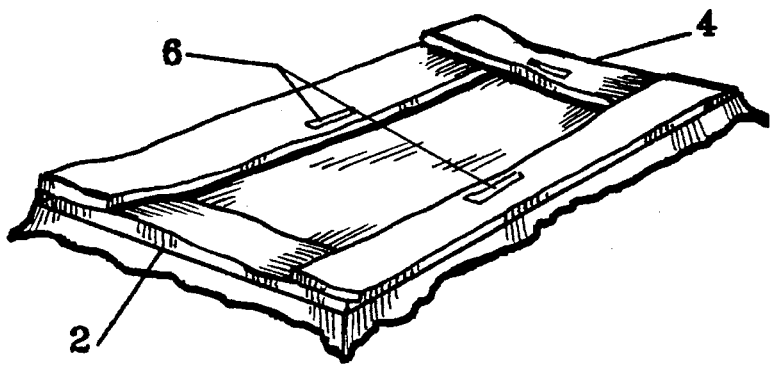
FIG. 10 illustrates the multiplicity of folds as shown in FIG. 5 when partially unfolded.

The components of the drape pack (7) are specifically positioned as in FIG. 1, then folded in reverse sequence to allow for sterile unfolding at designated stages of the surgical preparation process. FIG. 5 illustrates the folding sequence beginning with fan folds 1 *a, b, . . . n* of the craniotomy incise sheet (13) only. Next, fan folds 2 *a, b, . . . n* of the split sheet (11) are made allowing it to be placed on top of the multiple fan folds of the craniotomy incise sheet (13). Continuing folding consists of conventional folds 3 *a, b, . . . n*, 4 *a, b, . . . n*, and 5 *a, b, . . . n*, containing both the split sheet (11) and craniotomy incise sheet (13). With the previously mentioned folds made, the sheets now represent the size of the top surface of the table (5) as shown in FIG. 10. All of the multiple folds made represent the smallest area needed, approximately six inches wide, on the table (5) top surface (25) to prevent them from falling off or unfolding. Now viewing FIGS. 9, 8, and 7 in respective order, the final folds are made to the combined split sheet (11) and craniotomy incise sheet (13). Finally, the table cover sheet (10) is folded enabling it to be the outer most sheet of the drape pack (7).

The contents packaged inside the drape pack (7) are sterilized with only the outer surface of the table cover sheet (10) exposed when placed on the table (5). This allows for quick placement and positioning of the drape pack (7) on the table (5), the unfolding of the drape pack (7) for a sterile operating environment, and quick connection of operating devices.

Figure 6:
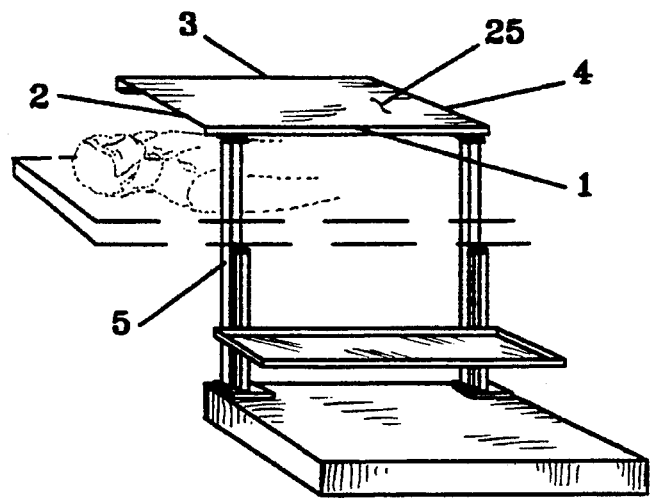
FIG. 6 illustrates one of several types of neurosurgical operating tables positioned over a patient.

Referring to FIG. 6, a neurosurgical overhead table (5) is configured with a nurse edge (1), head edge (2), side edge (3) and foot edge (4).

Figure 7:
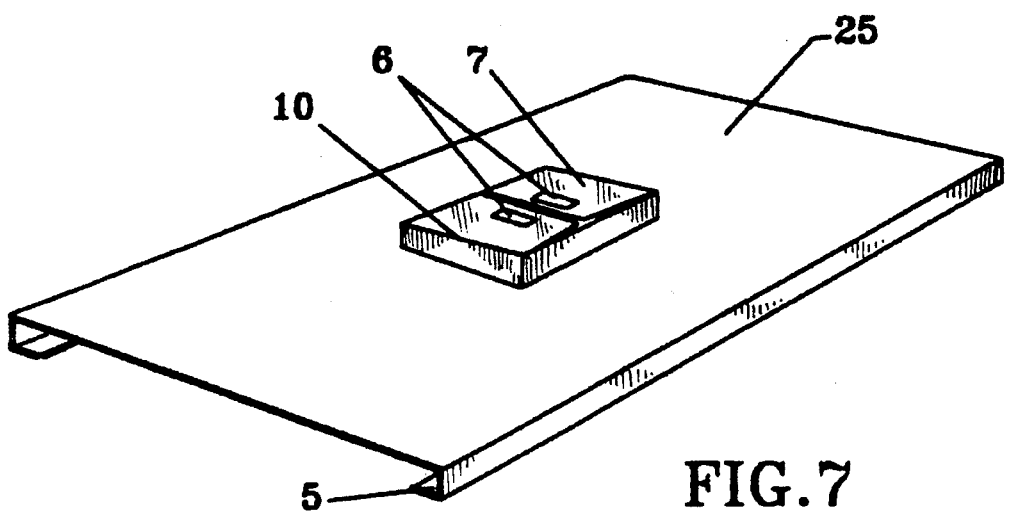
FIG. 7 illustrates the drape pack placed on a table ready for unfolding and preparation.
Figure 8:
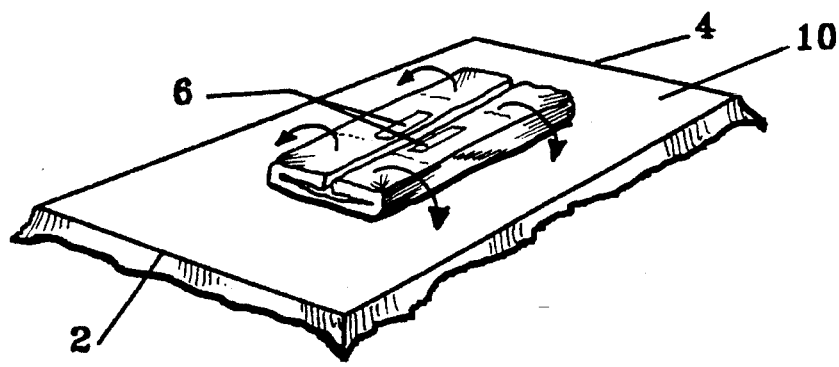
FIG. 8 illustrates the table cover sheet unfolded and the first unfolding of the craniotomy incise sheet and split sheet combination in the unfolding progression.
Figure 11:
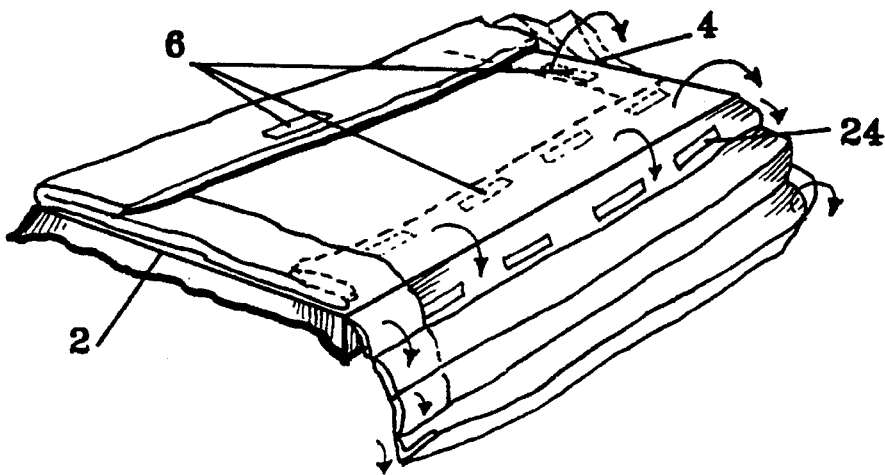
FIG. 11 illustrates the unfolding in progression just prior to instrument set up on the covered table surface.

The drape pack (7) is positioned centrally on the table (5) top surface (25), FIG. 7, is then unsealed and only the table cover sheet (10) is unfolded completely as indicated by printed directions (6) on the table cover sheet (10). The table cover sheet (10) is unfolded to the four edges of the table (5), FIG. 8, where the excess hangs over the edges a minimum of four inches thus providing a sterile working surface. FIG. 8, 9 and 10 illustrate the multiple folds containing the craniotomy incise sheet (13) and split sheet (11) unfolding to the four edges of the table (5). Next the multiple folds containing the craniotomy incise sheet (13) and split sheet (11) are unfolded completely over the nurse edge (1) and the foot edge (4), again following printed directions (6), FIG. 11. The combined folds, FIG. 12, containing the craniotomy incise sheet (13) and split sheet (11) which were previously unfolded to the side edge (3) and head edge (2) where the multiple folds are held by the foldings or can be held by perforated paper straps (12) which are attached to both sheets. VELCRO or other similar materials may also be used for the straps (12). This allows for the drapes to remain in a sterile manner while the covered top surface (25) of the table (5) is prepared with surgical instruments.

Figure 12:
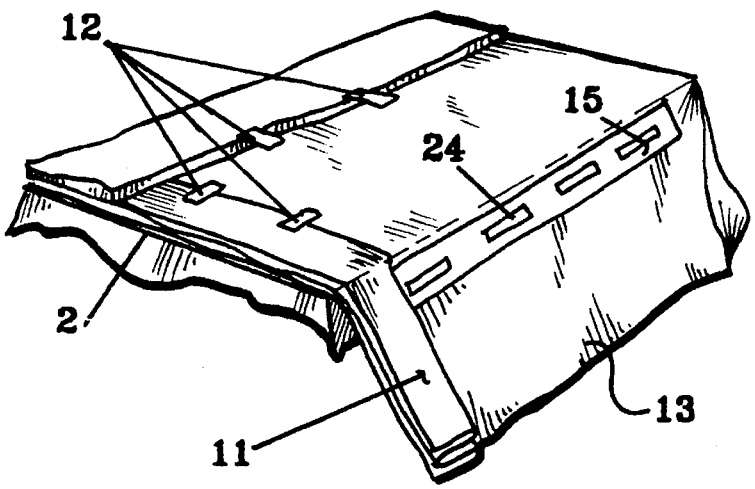
FIG. 12 illustrates the drape pack ready for instrument and device set up and positioning over the patient.

Next the patient is placed and positioned on the operating table, and the overhead table (5) is then positioned over the patient with the drape pack (7) prepared as illustrated in FIG. 12. Once the patient is positioned under the table (5) the drape pack (7) preparation can be completed in a speedy manner following the surgical preparation.

Figure 13:
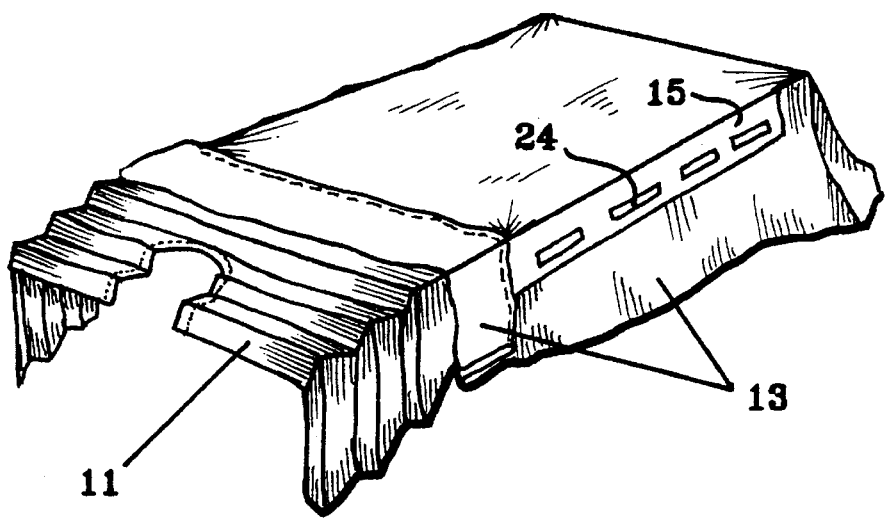
FIG. 13 illustrates the split sheet being unfolded over the surgical incision area of the patient.

After the surgical preparation to the patient's incision area is completed, the placing of four sterile towels to drape off the surgical site is done by the surgeon providing the first layer of sterility for the patient. Then the perforated paper straps (12), if used, are unfastened and the combined multiple folds containing the split sheet (11) and the craniotomy incise sheet (13) are unfolded completely over the side edge (3). The folded split sheet (11) which is pre-positioned on top of the folded craniotomy incise sheet (13) is in proper position at the head edge (2) of the table (5) to allow it to be unfolded by the surgeon, FIG. 13. This allows the surgeon to place the sticky self adhesive tape (20) edges of the split sheet (11) around the patient's head thus draping off the surgical site for the second layer of sterility while the multiple folds of the craniotomy incise sheet (13) remain at the head edge (2) of the table (5). The split sheet (11) normally has a sticky pressure sensitive adhesive tape (20) along the U-shape gap or fenestration of the split area in the head edge (2) of the split sheet (11) which allows forming the split sheet (11) around the area for surgery forming the exact surgical site.

Figure 14:
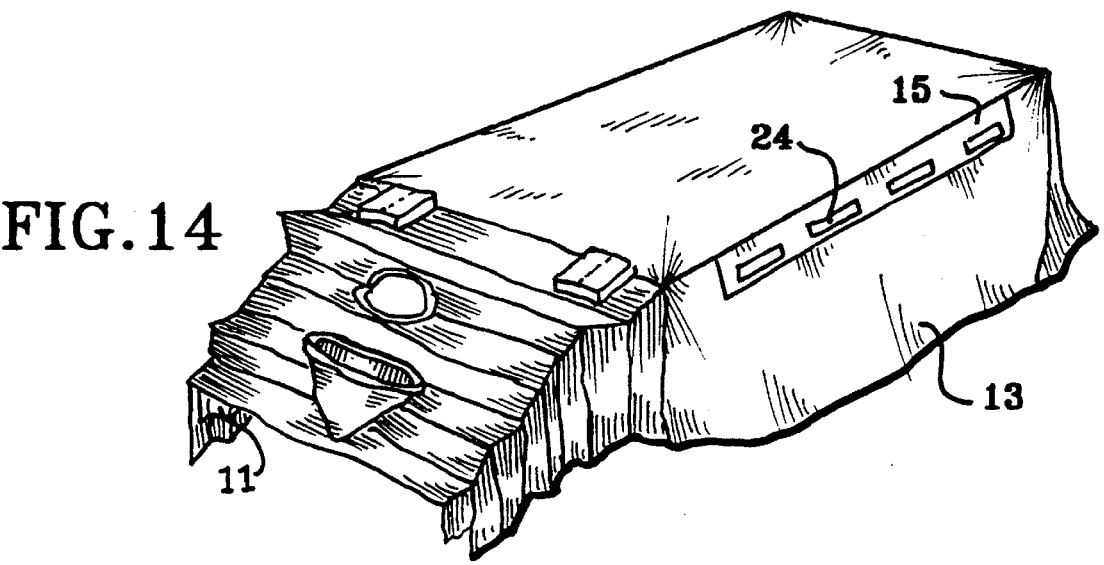
FIG. 14 illustrates the craniotomy incise sheet being unfolded over the split sheet and incision area forming the completed drape pack in use.

The craniotomy incise sheet (13) is next unfolded over the head edge (2) of the table (5) and placed over the split sheet (11) and incision area of the patient's head by the surgeon, FIG. 14. The craniotomy incise sheet (13) has a clear window (21), called a steri drape having a sticky surface, which is placed exactly over the area of the intended surgery. The craniotomy incise sheet (13) has a pocket (8) under the window (21) for the purpose of catching blood and irrigation fluids during the surgery. Again the craniotomy incise sheet (13) is properly assembled in the drape pack (7) allowing it to be placed, when unfolded, at the proper position on the patient's head, thus forming the third layer of sterility.

Figure 15:
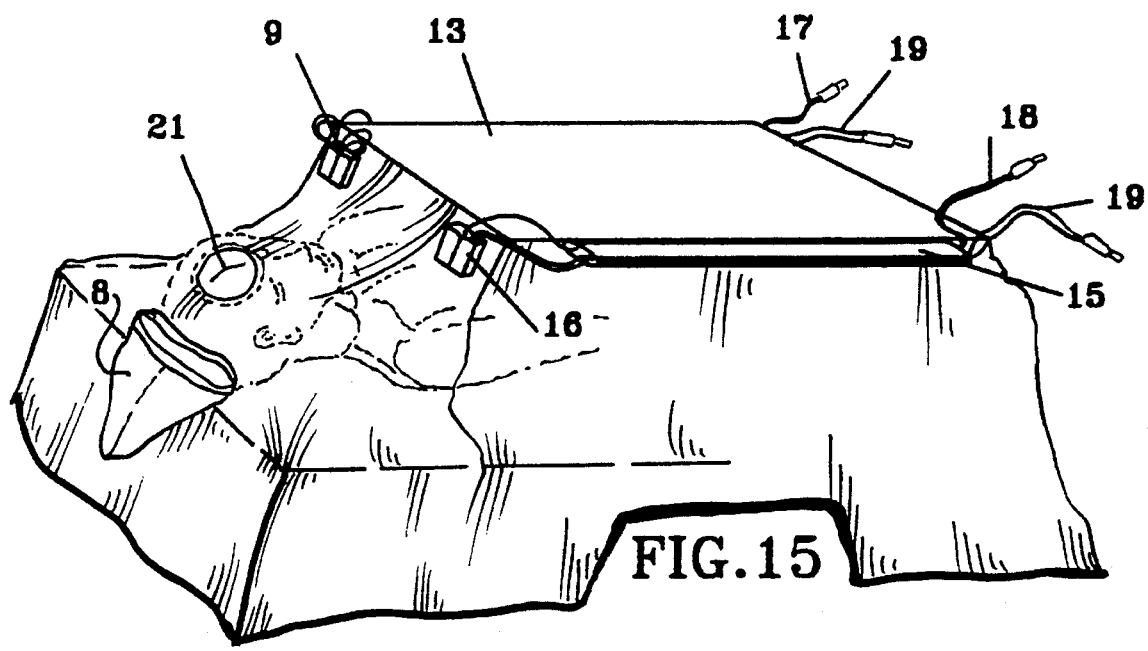
FIG. 15 illustrates the drape pack completely unfolded with the tubes, cords and surgical devices in place to start the operation.

FIG. 15 shows the completed process of the drape pack (7) with two channels (15) in use for holding bovie cord (18) and suction tubing (19) and holding bipolar cord (17) and suction tubing (19) respectively. The bipolar pocket (9) and bovie pocket (16) are very accessible. The patient is completely draped and ready for the incision to be made. The table (5) top surface (25) has ample room for instruments and devices.

What is claimed is:

1. An apparatus for covering and draping to provide a sterile surgical operating environment comprising an absorbent drape placed over a craniotomy incise sheet which is placed over a split sheet which is placed over a table cover thereby forming a drape pack which when folded up has the table cover as an outermost cover wherein the drape pack when placed on and located at a reference on a table can be unfolded such that the absorbent drape and the table cover are approximately centered over the table surface and the split sheet and craniotomy incise sheet can be draped over a patient at a head edge of the table; wherein the absorbent drape and the craniotomy incise sheet are joined at a surface except for a bovie channel and a bipolar channel therein; wherein the craniotomy incise sheet has a bovie pocket and a bipolar pocket wherein the bovie pocket has a compartment for holding a bovie device and a compartment for holding a suction tip and the bipolar pocket has a compartment for holding a bipolar forceps and a compartment for holding a suction tip; and wherein there is a strap attached to the split sheet and to the craniotomy incise sheet and the absorbent drape such that the craniotomy incise sheet and the split sheet may be retained at the head edge and a side edge of the table when partially unfolded.

2. The bovie channel and the bipolar channel as in claim 1 wherein the bovie channel has a bovie electric cord and a suction tube contained therein and the bipolar channel has a bipolar electric cord and a suction tube contained therein.

3. An apparatus for covering and draping to provide a sterile surgical operating environment comprising a craniotomy incise sheet which is placed over a split sheet which is placed over a table cover thereby forming a drape pack which when folded up has the table cover as an outermost cover wherein the drape pack when placed on and located at a reference on a table can be unfolded such that the table cover is approximately centered over the table surface and the split sheet and craniotomy incise sheet can be draped over a patient at a head edge of the table; wherein there is a strap used to hold the craniotomy incise sheet and the split sheet at the head edge and a side edge of the table when partially unfolded.

4. The apparatus as in claim 3 wherein there is a channel attached to the craniotomy incise sheet at a nurse edge and a channel attached to the craniotomy incise sheet at a side edge wherein the channels are the length of the nurse edge and side edge.

5. The apparatus as in claim 4 wherein the channel attached at the nurse edge has a bovie electric cord and a suction tube contained therein and the channel attached at the side edge has a bipolar cord and a suction tube contained therein.

6. The apparatus as in claim 3 wherein there is a bovie pocket and a bipolar pocket attached to the craniotomy incise sheet at a head edge wherein the bovie pocket has a compartment for holding a bovie device and a compartment for holding a suction tip and the bipolar pocket has a compartment for holding a bipolar forceps and a compartment for holding a suction tip wherein the bovie pocket and bipolar pocket are attached at the head edge in position to allow the bovie device, bipolar forceps and suction tips to be located adjacent to the operating site as the tubes and cords exit the channels.

7. An apparatus for covering and draping to provide a sterile surgical operating environment comprising:
   a. a craniotomy incise sheet which is placed over a split sheet which is placed over a table cover thereby forming a drape pack which when folded up has the table cover as an outermost cover wherein the drape pack when placed on and located at a reference on a table can be unfolded such that the table cover is approximately centered over the table surface and the split sheet and craniotomy incise sheet can be draped over a patient at a head edge of the table;
   b. the craniotomy incise sheet is fan folded to the head edge, the split sheet is fan folded to the head edge and laid on the craniotomy incise sheet fan folds, the craniotomy incise sheet and split sheet are folded to the side edge, the craniotomy incise sheet and split sheet are folded to the nurse edge, the craniotomy incise sheet and split sheet are folded to a foot edge, and the combination of folds is further alternatively folded with the table cover sheet to form the drape pack in a folded configuration.

8. The apparatus as in claim 7 wherein there is a channel attached to the craniotomy incise sheet at a nurse edge and a channel attached to the craniotomy incise sheet at a side edge wherein the channels are the length of the nurse edge and side edge.

9. The apparatus as in claim 8 wherein the channel attached at the nurse edge has a bovie electric cord and a suction tube contained therein and the channel attached at the side edge has a bipolar cord and a suction tube contained therein.

10. The apparatus as in claim 7 wherein there is a bovie pocket and a bipolar pocket attached to the craniotomy incise sheet at a head edge wherein the bovie pocket has a compartment for holding a bovie device and a compartment for holding a suction tip and the bipolar pocket has a compartment for holding a bipolar forceps and a compartment for holding a suction tip wherein the bovie pocket and bipolar pocket are attached at the head edge in position to allow the bovie device, bipolar forceps and suction tips to be located adjacent to the operating site as the tubes and cords exit the channels.

11. An apparatus for use in providing a sterile surgical operating environment for complicated neurosurgical procedures comprising a craniotomy incise sheet having a plurality of formable conduit of flexible material with attachment means to a main sheet along a longitudinal border which is attached longitudinally and parallel to the patients body and a plurality of pocket members with dual device compartments having self adhesive attachment means to the craniotomy incise sheet.

12. The apparatus of claim 11 in combination with a split sheet forming a drape pack.

13. The apparatus of claim 12 in combination with a table cover sheet forming a drape pack.

14. The apparatus of claim 13 wherein a plurality of electrical cables and a plurality of tubes are contained in the formable conduit.

15. The apparatus of claim 12 wherein a plurality of electrical cables and a plurality of tubes are contained in the formable conduit.

16. An apparatus for covering and draping to provide a sterile surgical operating environment comprising a craniotomy incise sheet which has a channel attached to the craniotomy incise sheet at a nurse edge and a channel attached to the craniotomy incise sheet at a side edge wherein the channel attached at the nurse edge has a bovie electric cord and a suction tube contained therein and the channel attached at the side has a bipolar cord and a suction tube contained therein.

\* \* \* \* \*